(12) United States Patent
Schmetz-Schagen et al.

(10) Patent No.: US 10,317,805 B2
(45) Date of Patent: Jun. 11, 2019

(54) METHOD FOR MONITORING A CHARACTERISTIC OF ILLUMINATION FROM A METROLOGY APPARATUS

(71) Applicant: ASML Netherlands B.V., Veldhoven (NL)

(72) Inventors: Jolanda Theodora Josephina Schmetz-Schagen, Son en Breugel (NL); Hugo Augustinus Joseph Cramer, Eindhoven (NL); Armand Eugene Albert Koolen, Nuth (NL); Bastiaan Onne Fagginger Auer, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/842,958

(22) Filed: Dec. 15, 2017

(65) Prior Publication Data

US 2018/0173113 A1 Jun. 21, 2018

(30) Foreign Application Priority Data

Dec. 16, 2016 (EP) .................................... 16204662

(51) Int. Cl.
*G03F 9/00* (2006.01)
*G03F 7/20* (2006.01)
*G01N 21/956* (2006.01)
*G01B 11/02* (2006.01)
*G01M 11/02* (2006.01)

(52) U.S. Cl.
CPC ........ *G03F 7/70641* (2013.01); *G01B 11/028* (2013.01); *G01M 11/0264* (2013.01); *G01N 21/956* (2013.01); *G03F 7/70616* (2013.01); *G03F 7/70625* (2013.01); *G03F 7/70633* (2013.01); *G03F 9/7026* (2013.01)

(58) Field of Classification Search
CPC ............. G03F 7/70633; G03F 7/70641; G03F 7/70616; G03F 7/70626
USPC .............................................. 355/52, 53, 55
See application file for complete search history.

(56) References Cited

U.S. PATENT DOCUMENTS

| 7,630,070 B2 | 12/2009 | Hugers |
| 7,869,022 B2 | 1/2011 | Van Boxmeer et al. |
| 7,880,889 B2 | 2/2011 | Den Boef |
| 8,994,921 B2 | 3/2015 | Van Boxmeer et al. |

(Continued)

FOREIGN PATENT DOCUMENTS

| WO | WO 2012/126718 A1 | 9/2012 |
| WO | WO 2014/082938 A1 | 6/2014 |

OTHER PUBLICATIONS

Hinnen, et al., "Scatterometry-based on-product focus measurement and monitoring," ASMC Semi Advanced Semiconductor Manufacturing Conference, May 1, 2013; pp. 352-359.

(Continued)

*Primary Examiner* — Hung Nguyen
(74) *Attorney, Agent, or Firm* — Sterne, Kessler, Goldstein & Fox P.L.L.C.

(57) ABSTRACT

A method for monitoring a characteristic of illumination from a metrology apparatus includes using the metrology apparatus to acquire a pupil image at different focus settings of the metrology apparatus and calculating an asymmetry value for each acquired pupil image, where each pupil image is acquired on at least one edge of a target of a substrate.

19 Claims, 4 Drawing Sheets

(56) References Cited

U.S. PATENT DOCUMENTS

| | | |
|---|---|---|
| 2006/0033921 A1 | 2/2006 | Den Boef et al. |
| 2006/0066855 A1 | 3/2006 | Boef et al. |
| 2008/0151228 A1 | 6/2008 | Hugers |
| 2010/0201963 A1 | 8/2010 | Cramer et al. |
| 2010/0328655 A1 | 12/2010 | Den Boef |
| 2011/0027704 A1 | 2/2011 | Cramer et al. |
| 2011/0043791 A1 | 2/2011 | Smilde et al. |
| 2011/0069292 A1 | 3/2011 | Den Boef |
| 2012/0044470 A1 | 2/2012 | Smilde et al. |
| 2012/0123581 A1 | 5/2012 | Smilde et al. |
| 2013/0258310 A1 | 10/2013 | Smilde et al. |
| 2013/0271740 A1 | 10/2013 | Quintanilha |
| 2013/0308142 A1* | 11/2013 | Straaijer ............... G01B 11/24 356/625 |
| 2014/0139814 A1 | 5/2014 | Cramer et al. |
| 2015/0145151 A1* | 5/2015 | Van Der Schaar ......................... G03F 7/70633 257/797 |
| 2016/0123894 A1* | 5/2016 | Fu ..................... G01B 11/0616 356/615 |
| 2016/0363871 A1 | 12/2016 | Van Oosten et al. |
| 2017/0176714 A1 | 6/2017 | Van Der Zouw |

OTHER PUBLICATIONS

International Search Report and Written Opinion of the International Searching Authority directed to related International Patent Application No. PCT/EP2017/080476, dated Feb. 12, 2018; 14 pages.

\* cited by examiner

METHOD FOR MONITORING A CHARACTERISTIC OF ILLUMINATION FROM A METROLOGY APPARATUS

FIELD

The present invention relates to a method for monitoring a characteristic of illumination from a metrology apparatus. The invention may be applied for example in an inspection apparatus.

BACKGROUND

A lithographic process is one that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive material (resist) provided on the substrate. Stepping and/or scanning movements can be involved, to repeat the pattern at successive target portions across the substrate. It is also possible to transfer the pattern from the patterning device to the substrate by imprinting the pattern onto the substrate.

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay (the accuracy of alignment between patterns formed in different patterning steps, for example between two layers in a device) and defocus of the lithographic apparatus. Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target structure by iterative approaches such as rigorous coupled wave analysis or finite element methods; library searches; and principal component analysis.

Methods and apparatus for determining structure parameters are, for example, disclosed in WO 2012126718. Methods and scatterometers are also disclosed in US20110027704A1, US2006033921A1 and US2010201963A1. In addition to scatterometry to determine parameters of a structure made in one patterning step, the methods and apparatus can be applied to perform diffraction-based overlay measurements. Diffraction-based overlay metrology using dark-field image detection of the diffraction orders enables overlay measurements on smaller targets. Examples of dark-field imaging metrology can be found in international patent applications US2010328655 A1 and US2011069292 A1. Further developments of the technique have been described in published patent applications US20110027704A, US20110043791A, US20120044470A US20120123581A, US20130258310A, US20130271740A and WO2013178422A1. The above documents generally describe measurement of overlay though measurement of asymmetry of targets. Methods of measuring dose and focus of a lithographic apparatus using asymmetry measurements are disclosed in documents WO2014082938 A1 and US2014/0139814A1, respectively. The contents of all the mentioned applications are also incorporated herein by reference. The invention is not limited in application to any particular type of inspection apparatus, or even to inspection apparatuses generally.

A common problem in inspection apparatuses is one of controlling focusing of the optical system onto a target. Many systems require real-time control of focus of the optical system, within very tight tolerances. A focus control arrangement for a scatterometer of the type described above is disclosed for example in published patent application US20080151228A. Light reflected from the target is imaged with deliberate focus error on two photodetectors. Comparing the light intensity between the two photodetectors allows an indication of defocus to be obtained, and the direction of defocus to be identified. The contents of that application are incorporated herein by reference.

It is desirable to improve accuracy of monitoring a characteristic of illumination from a metrology apparatus. For example, it is desirable to improve the focus accuracy that can be achieved.

SUMMARY

According to the present invention, there is provided a method for monitoring a characteristic of illumination from a metrology apparatus, the method comprising:

using the metrology apparatus to acquire a pupil image at different focus settings of the metrology apparatus; and calculating an asymmetry value for each acquired pupil image; wherein each pupil image is acquired on at least one edge of a target of a substrate.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF EXEMPLARY EMBODIMENTS

Figure 1:
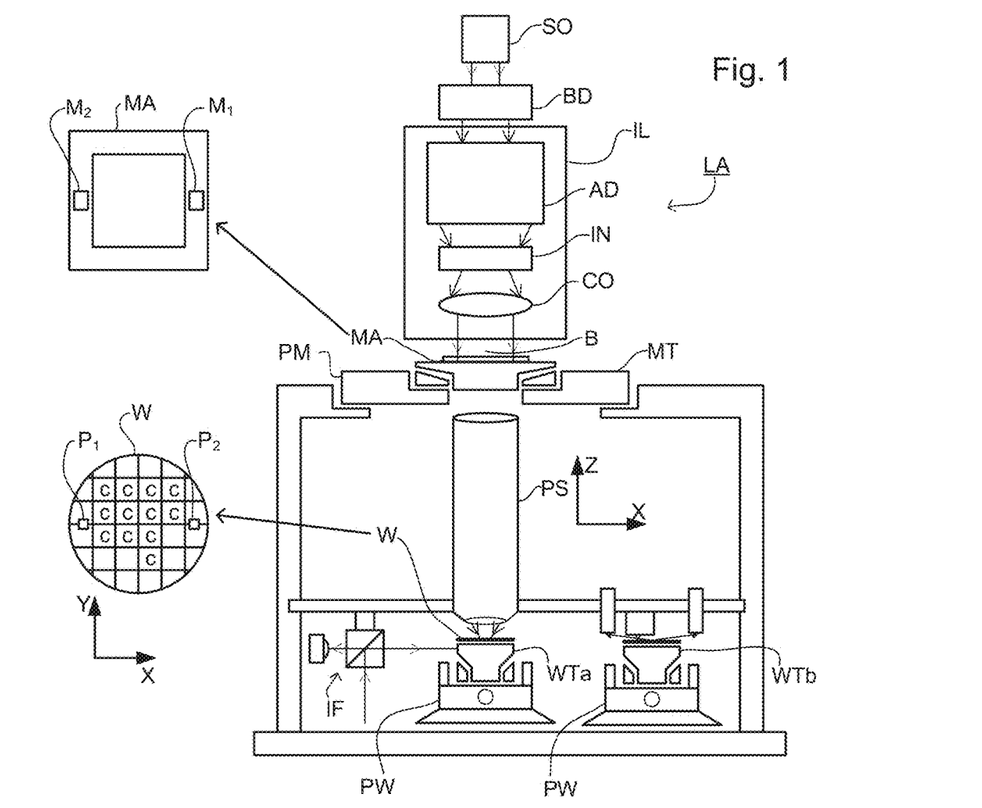
FIG. 1 depicts a lithographic apparatus.

FIG. 1 schematically depicts a lithographic apparatus LA. The lithographic apparatus LA comprises:
- an illumination system (illuminator) IL configured to condition a radiation beam B (e.g. UV radiation or DUV radiation).
- a support structure (e.g. a mask table) MT constructed to support a patterning device (e.g. a mask) MA and connected to a first positioner PM configured to accurately position the patterning device MA in accordance with certain parameters;
- a substrate table (e.g. a wafer table) WT constructed to hold a substrate (e.g. a resist-coated wafer) W and connected to a second positioner PW configured to accurately position the substrate W in accordance with certain parameters; and
- a projection system (e.g. a refractive projection lens system) PS configured to project a pattern imparted to the radiation beam B by patterning device MA onto a target portion C (e.g. comprising one or more dies) of the substrate W.

The illumination system IL may include various types of optical components, such as refractive, reflective, magnetic, electromagnetic, electrostatic or other types of optical components, or any combination thereof, for directing, shaping, or controlling radiation.

The support structure MT supports, i.e. bears the weight of, the patterning device MA. It holds the patterning device MA in a manner that depends on the orientation of the patterning device MA, the design of the lithographic apparatus LA, and other conditions, such as for example whether or not the patterning device MA is held in a vacuum environment. The support structure MT can use mechanical, vacuum, electrostatic or other clamping techniques to hold the patterning device MA. The support structure MT may be a frame or a table, for example, which may be fixed or movable as required. The support structure MT may ensure that the patterning device MA is at a desired position, for example with respect to the projection system PS. Any use of the terms "reticle" or "mask" herein may be considered synonymous with the more general term "patterning device."

The term "patterning device" used herein should be broadly interpreted as referring to any device that can be used to impart a radiation beam B with a pattern in its cross-section such as to create a pattern in a target portion C of the substrate W. It should be noted that the pattern imparted to the radiation beam B may not exactly correspond to the desired pattern in the target portion C of the substrate W, for example if the pattern includes phase-shifting features or so called assist features. Generally, the pattern imparted to the radiation beam B will correspond to a particular functional layer in a device being created in the target portion C, such as an integrated circuit.

The patterning device MA may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the lithographic apparatus LA is of a transmissive type (e.g. employing a transmissive mask). Alternatively, the lithographic apparatus LA may be of a reflective type (e.g. employing a programmable mirror array of a type as referred to above, or employing a reflective mask).

The lithographic apparatus LA may be of a type having two (dual stage) or more substrate tables WTa, WTb (and/or two or more mask tables). In such "multiple stage" machines the additional tables may be used in parallel, or preparatory steps may be carried out on one or more tables while one or more other tables are being used for exposure.

The lithographic apparatus LA may also be of a type wherein at least a portion of the substrate W may be covered by a liquid having a relatively high refractive index, e.g. water, so as to fill a space between the projection system PS and the substrate W. An immersion liquid may also be applied to other spaces in the lithographic apparatus LA, for example, between the patterning device MA and the projection system PS. Immersion techniques are well known in the art for increasing the numerical aperture of the projection system PS. The term "immersion" as used herein does not mean that a structure, such as a substrate W, must be submerged in liquid, but rather only means that liquid is located between the projection system PS and the substrate W during exposure.

Referring to FIG. 1, the illumination system IL receives a radiation beam B from a radiation source SO. The radiation source SO and the lithographic apparatus LA may be separate entities, for example when the radiation source SO is an excimer laser. In such cases, the radiation source SO is not considered to form part of the lithographic apparatus LA and the radiation beam B is passed from the radiation source SO to the illumination system IL with the aid of a beam delivery system BD comprising, for example, suitable directing mirrors and/or a beam expander. In other cases the radiation source SO may be an integral part of the lithographic apparatus LA, for example when the radiation source SO is a mercury lamp. The radiation source SO and the illumination system IL, together with the beam delivery system BD if required, may be referred to as a radiation system.

The illumination system IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illumination system IL can be adjusted. In addition, the illumination system IL may comprise various other components, such as an integrator IN and a condenser CO. The illumination system IL may be used to condition the radiation beam B, to have a desired uniformity and intensity distribution in its cross-section.

The radiation beam B is incident on the patterning device (e.g., mask) MA, which is held on the support structure (e.g., mask table) MT, and is patterned by the patterning device MA. Having traversed the patterning device MA, the radiation beam B passes through the projection system PS, which focuses the radiation beam B onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the patterning device MA with respect to the path of the radiation beam B, e.g. after mechanical retrieval from a mask library, or during a scan. In general, movement of the support structure MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the support structure MT may be connected to a short-stroke actuator only, or may be fixed. Patterning device MA and substrate W may be aligned using mask alignment marks $M_1$, $M_2$ and substrate alignment marks $P_1$, $P_2$. Although the substrate alignment marks $P_1$, $P_2$ as illustrated occupy dedicated target portions C, they may be located in spaces between target portions C (these are known as scribe-lane alignment marks). Similarly, in situations in which more than one die is provided on the patterning device MA, the mask alignment marks $M_1$, $M_2$ may be located between the dies.

The depicted lithographic apparatus LA could be used in at least one of the following modes:

1. In step mode, the support structure MT and the substrate table WT are kept essentially stationary, while an entire pattern imparted to the radiation beam B is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the support structure MT and the substrate table WT are scanned synchronously while a pattern imparted to the radiation beam B is projected onto a target portion C (i.e. a single dynamic exposure). The velocity and direction of the substrate table WT relative to the mask table MT may be determined by the (de-)magnification and image reversal characteristics of the projection system PS. In scan mode, the maximum size of the exposure field limits the width (in the non-scanning direction) of the target portion C in a single dynamic exposure, whereas the length of the scanning motion determines the height (in the scanning direction) of the target portion C.

3. In another mode, the support structure MT is kept essentially stationary holding a programmable patterning device MA, and the substrate table WT is moved or scanned while a pattern imparted to the radiation beam B is projected onto a target portion C. In this mode, generally a pulsed radiation source SO is employed and the programmable patterning device MA is updated as required after each movement of the substrate table WT or in between successive radiation pulses during a scan. This mode of operation can be readily applied to maskless lithography that utilizes programmable patterning device MA, such as a programmable mirror array of a type as referred to above.

Combinations and/or variations on the above described modes of use or entirely different modes of use may also be employed.

Figure 2:
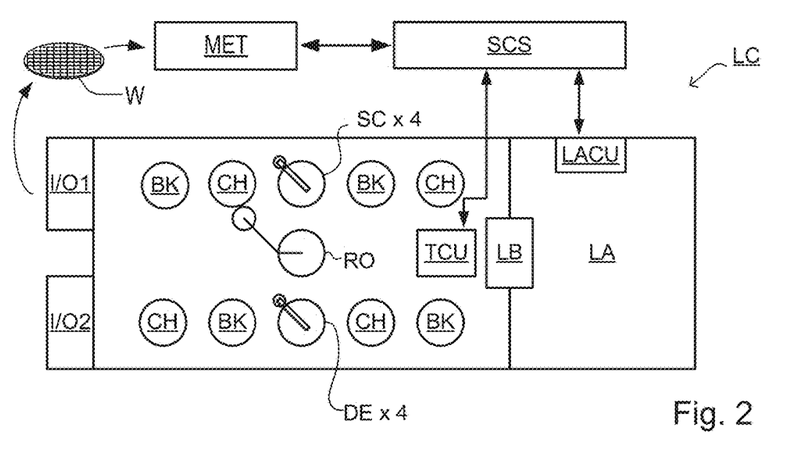
FIG. 2 depicts a lithographic cell or cluster in which an inspection apparatus according to the present invention may be used.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates W from input/output ports I/O1, I/O2, moves them between the different process apparatus and delivers then to the loading bay LB of the lithographic apparatus LA. These devices, which are often collectively referred to as the track, are under the control of a track control unit TCU which is itself controlled by the supervisory control system SCS, which also controls the lithographic apparatus LA via lithography control unit LACU. Thus, the different apparatus can be operated to maximize throughput and processing efficiency.

In order that the substrates W that are exposed by the lithographic apparatus LA are exposed correctly and consistently, it is desirable to inspect exposed substrates W to measure properties such as overlay errors between subsequent layers, line thicknesses, critical dimensions (CD), etc. Accordingly a manufacturing facility in which lithographic cell LC is located also includes metrology system MET which receives some or all of the substrates W that have been processed in the lithographic cell LC. Metrology results are provided directly or indirectly to the supervisory control system SCS. If errors are detected, adjustments may be made to exposures of subsequent substrates W, especially if the inspection can be done soon and fast enough that other substrates W of the same batch are still to be exposed. Also, already exposed substrates W may be stripped and reworked to improve yield, or discarded, thereby avoiding performing further processing on substrates W that are known to be faulty. In a case where only some target portions C of a substrate W are faulty, further exposures can be performed only on those target portions C which are good.

Within metrology system MET, an inspection apparatus is used to determine the properties of the substrates W, and in particular, how the properties of different substrates W or different layers of the same substrate W vary from layer to layer. The inspection apparatus may be integrated into the lithographic apparatus LA or the lithographic cell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates W and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
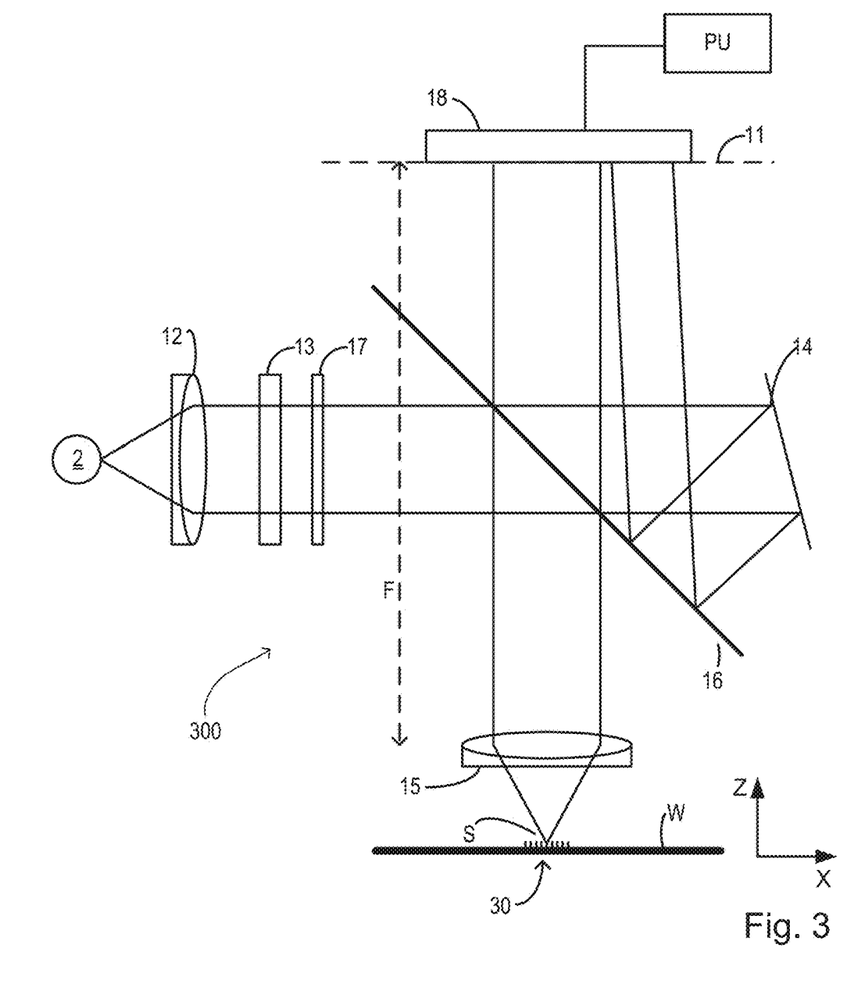
FIG. 3 depicts a known inspection apparatus arranged to perform angle-resolved scatterometry, as an example of an optical system in which a focus monitoring arrangement according to the present invention may be applied.

FIG. 3 depicts a known scatterometer 300. In this device, the radiation emitted by illumination source 2 is collimated using lens system 12 and transmitted through interference filter 13 and polarizer 17, reflected by partially reflecting surface 16 and is focused into a spot S on substrate W via a microscope objective lens 15, which has a high numerical aperture (NA), preferably at least 0.9 and more preferably at least 0.95. Immersion scatterometers may even have lenses with numerical apertures over 1.

As in the lithographic apparatus LA, one or more substrate tables WT may be provided to hold the substrate W during measurement operations. The substrate tables WT may be similar or identical in form to the substrate tables WTa, WTb of FIG. 1. In an example where the inspection apparatus is integrated with the lithographic apparatus LA, they may even be the same substrate tables WT. Coarse and fine positioners may be provided to a second positioner PW configured to accurately position the substrate W in relation to a measurement optical system. Various sensors and actuators are provided for example to acquire the position of a target of interest, and to bring it into position under the objective lens 16. Typically many measurements will be made on targets at different locations across substrate W. The substrate table WT can be moved in X and Y directions to acquire different targets, and in the Z direction to obtain a desired focusing of the optical system on the target. It is convenient to think and describe operations as if the objective lens 15 and optical system being brought to different locations on the substrate W, when in practice the optical system remains substantially stationary and only the substrate W moves. Provided the relative position of the substrate W and the optical system is correct, it does not matter in principle which one of those is moving in the real world, or if both are moving.

The reflected radiation then passes through partially reflecting surface 16 into a detector 18 in order to have the scatter spectrum detected. The detector 18 may be located in the back-projected pupil plane 11, which is at the focal length of the objective lens 15, however the pupil plane may instead be re-imaged with auxiliary optics (not shown) onto the detector 18. The pupil plane is the plane in which the radial position of radiation defines the angle of incidence and the angular position defines azimuth angle of the radiation. The detector 18 is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the partially reflecting surface 16 part of it is transmitted through the partially reflecting surface 16 as a reference beam towards a reference mirror 14. The reference beam is then projected onto a different part of the same detector 18 or alternatively on to a different detector (not shown).

A set of interference filters 13 is available to select a wavelength of interest in the range of, say, 405-790 nm or even lower, such as 200-300 nm. The interference filter 13 may be tunable rather than comprising a set of different filters. A grating could be used instead of interference filters 13. An aperture stop or spatial light modulator (not shown) may be provided in the illumination path to control the range of angle of incidence of radiation on the target.

The detector 18 may measure the intensity of scattered light at a single wavelength (or narrow wavelength range), the intensity separately at multiple wavelengths or integrated over a wavelength range. Furthermore, the detector 18 may separately measure the intensity of transverse magnetic- and transverse electric-polarized light and/or the phase difference between the transverse magnetic- and transverse electric-polarized light.

The substrate target 30 on substrate W may be a 1-D grating, which is printed such that after development, the bars are formed of solid resist lines. The substrate target 30 may be a 2-D grating, which is printed such that after development, the grating is formed of solid resist pillars or vias in the resist. The bars, pillars or vias may alternatively be etched into the substrate W. This pattern is sensitive to chromatic aberrations in the lithographic apparatus LA, particularly the projection system PS, and illumination symmetry and the presence of such aberrations will manifest themselves in a variation in the printed grating. Accordingly, the scatterometry data of the printed gratings is used to reconstruct the gratings. The parameters of the 1-D grating, such as line widths and shapes, or parameters of the 2-D grating, such as pillar or via widths or lengths or shapes, may be input to the reconstruction process, performed by processor PU, from knowledge of the printing step and/or other scatterometry processes.

In addition to measurement of parameters by reconstruction, angle resolved scatterometry is useful in the measurement of asymmetry of features in product and/or resist patterns. A particular application of asymmetry measurement is for the measurement of overlay, where the substrate target 30 comprises one set of periodic features superimposed on another. The concepts of asymmetry measurement using the instrument of for instance FIG. 3 are described for example in published patent application US2006066855A1. Simply stated, while the positions of the diffraction orders in the diffraction spectrum of the target are determined only by the periodicity of the target, asymmetry in the diffraction spectrum is indicative of asymmetry in the individual features which make up the target. In the instrument of FIG. 3, where detector 18 may be an image sensor, such asymmetry in the diffraction orders appears directly as asymmetry in the pupil image recorded by detector 18. This asymmetry can be measured by digital image processing in processor PU, and calibrated against known values of overlay.

Figure 4:
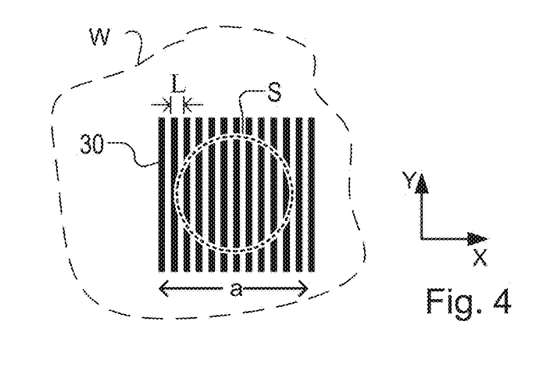
FIG. 4 illustrates the relationship between an illumination spot and a target grating in an example of the known scatterometers.

FIG. 4 illustrates a plan view of a typical substrate target 30, and the extent of illumination spot S in the scatterometer of FIG. 3. To obtain a diffraction spectrum that is free of interference from surrounding structures, the target 30 in the known method is a grating larger than the diameter of the illumination spot S. The diameter of spot S may be over 10 or 20 µm and the grating width a and length may be 30 or 40 µm square, may be less than 2 µm and the grating width and length maybe be 5 µm. The substrate target 30 may be periodic with a pitch L. The grating in other words is 'underfilled' by the illumination, and the diffraction signal is free from interference by product features and the like outside the target grating itself. The illumination arrangement comprising the illumination source 2, the lens system 12, the interference filter 13 and the polarizer 17 may be configured to provide illumination of a uniform intensity across a pupil plane of objective lens 15. Alternatively, but including an aperture in the illumination path, illumination may be restricted to on axis or off axis directions. As described in prior applications cited above, a modified scatterometer can use so-called dark field imaging to capture diffracted radiation from several smaller targets, all falling within the same illumination spot S.

Regardless of the type of inspection apparatus, it is generally required to provide an automatic system for monitoring and adjusting focus of an optical system such as the system that forms the scatterometer 300 in FIG. 3. If the spot S is not focused, then the illumination will fall on features other than the target 30, and the collected radiation will not allow an accurate measurement of the properties of the target 30. As mentioned already, focusing arrangements are known which pass a beam of radiation through the optical system and use some kind of detector system to obtain a signal representing focus error. For example, in published patent application US20080151228A, light reflected from the target is imaged onto two photodetectors with different focus offsets. Comparing the focused light intensity between the two photodetectors allows an indication of defocus of the optical system to be obtained, and the direction of defocus to be identified. The US patent application illustrates various simple photodetectors that may be used to obtain a measure of spot area. The contents of that patent application are incorporated herein by reference. Other types of focus arrangement can be envisaged, and the present disclosure is not limited to the technique of US 20080151228 A.

An embodiment of the invention relates to a method for monitoring a characteristic of illumination from a metrology apparatus. A metrology apparatus may also be known as an inspection apparatus. The metrology apparatus may be provided as part of the metrology system MET shown in FIG. 2. The scatterometer 300 shown in FIG. 3 is an example of a metrology apparatus according to an embodiment of the invention.

In the example of the scatterometer 300 shown in FIG. 3, the illumination is provided from the illumination source 2. The illumination is focused into the spot S on the target 30. The method of the invention is for monitoring a characteristic of this illumination.

In an embodiment, the method comprises using the metrology apparatus to acquire a pupil image 31 at different focus settings of the metrology apparatus. Each focus setting of the metrology apparatus corresponds to the metrology apparatus being used to attempt to focus the spot S at a different position in the Z-direction (i.e. the vertical direction). The Z-direction is perpendicular to the plane of the target 30.

In particular, each focus setting may correspond to a set defocus of the metrology apparatus. A defocus of zero corresponds to when the metrology apparatus is used to try to focus the spot S on the target 30 at the level of the target 30. Other focus settings corresponding to non-zero defocus values correspond to when the metrology apparatus is used to try to focus the spot S a certain distance (the defocus value) above or below the level of the target 30.

It may be that the focus setting with a zero defocus value is the optimum focus setting of the metrology apparatus. However, it may be that a better focus is acquired when using a different focus setting of the metrology apparatus. The method of the present invention can be used to determine which focus setting (or between which focus settings) the best focus of the spot S on the target 30 can be achieved.

In an embodiment, each pupil image 31 is acquired on at least one edge 32 of the target 30. The target 30 is a target of a substrate W. the target 30 may be part of the substrate W that is primarily used for a function other than calibrating the focus of the metrology apparatus. For example, the target 30 may correspond to the substrate alignment marks $P_1$, $P_2$ illustrated in FIG. 1. In an embodiment the target 30 is located in the spaces between the target portions C of the substrate W. For example, in an embodiment the target 30 is positioned in a scribe lane of the substrate W.

The metrology apparatus is used to inspect characteristics or properties of the substrate W. For example, the metrology apparatus can be used to measure the quality or accuracy of one or more patterns formed in layers of the substrate W. According to the invention, the characteristic of illumination from the metrology apparatus is monitored by acquiring pupil images 31 on the target 30 of the substrate W that is to be inspected by the metrology apparatus. This is different from known techniques in which focus of a metrology apparatus may be calibrated using measurement of a fiducial that is part of the metrology apparatus.

In particular, if the focus of the metrology apparatus is calibrated by making measurements of a fiducial of the metrology apparatus itself, then the results of this calibration do not take into account the different applications for which the metrology apparatus is to be used. For example, the calibration of the metrology apparatus does not take into account the properties of the substrate W which is to be inspected by the metrology apparatus.

Such a method of calibration may provide a sufficient level of accuracy for the focus of the metrology apparatus if the spot S formed by the metrology apparatus is intended to be sufficiently large and measures large targets (for example 40×40 μm). However, for newer generation metrology apparatuses, the metrology apparatus is designed to focus the illumination into a spot S having a smaller size and measure on smaller targets for example 4.5×4.5 μm targets. For example, in an embodiment each pupil image 31 is formed by illuminating the target 30 with an illumination spot S having a diameter of at most 20 μm. In an embodiment, each pupil image 31 is formed by illuminating the target 30 with an illumination spot S having a diameter of at most 10 μm, at most 5 μm, and optionally at most 2 μm. For example, according to specific examples, the metrology apparatus has an illumination spot S with a diameter of 1.9 μm, or 1.8 μm.

Calibrating the focus of the metrology apparatus using a fiducial of the metrology apparatus may not provide sufficient accuracy of the focus of the metrology apparatus. This may be a particularly severe problem for a metrology apparatus with a small illumination spot size, although the invention is not limited to use with a metrology apparatus having a small illumination spot size. The invention can be used to improve the monitoring of a characteristic of illumination from a metrology apparatus having any spot size.

As explained above, in an embodiment each pupil image 31 is acquired on at least one edge 32 of the target 30 of the substrate W. By acquiring each pupil image 31 on the target 30 of the substrate W (instead of using a fiducial of the metrology apparatus), characteristics of illumination from the metrology apparatus can be monitored more accurately. For example, in an embodiment, the focus of the illumination spot S from the metrology apparatus can be calibrated or controlled more accurately (i.e. within a smaller tolerance).

In particular, by acquiring each pupil image 31 at the target 30 of the substrate W, the particular properties or characteristics of that substrate W can be taken into account. For example, the calibration of the focus of the metrology apparatus takes into account each application of the metrology apparatus. This makes tighter focusing possible. Instead of using of an application-independent focus set up, in an embodiment the focus set up of the metrology apparatus is application-dependent. As a result, properties of the substrate W such as layer thicknesses, which can contribute to CD signals, can be taken into account in the focus set up of the metrology apparatus.

Furthermore, the method for monitoring the characteristic of illumination from a metrology apparatus according to an embodiment of the invention is more reliable than known methods. In particular, positioning of a small illumination spot S at the edge of a fiducial of the metrology apparatus can go wrong. For example, the edge of the fiducial has a certain roughness. This roughness can result in failure of the calibration of the focus of the spot S of the metrology apparatus. In an embodiment, the edge of the target 30 of the substrate W is less rough than the edge of the fiducial of the metrology apparatus. Accordingly, the illuminations spot S of the metrology apparatus can be positioned more reliably on the edge 32 of the target 30. This improves the reliability of monitoring a characteristic of illumination from the metrology apparatus.

Figure 5:
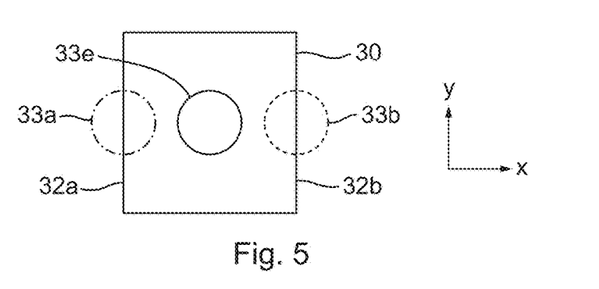
FIG. 5 is a schematic diagram of locations on a target at which a pupil is measured according to an embodiment of the invention.

FIG. 5 is a diagram showing locations on the target 30 at which the pupil images 31 are acquired. FIG. 5 depicts the target 30 having edges 32a, 32b extending in the Y-direction. Each circle shown in FIG. 5 represents a spot location 33 at which a pupil image 31 is acquired. FIG. 5 shows that a pupil image 31 may be acquired at three spot locations 33 of the target 30. The spot location 33 is the position on the target 30 illuminated by the spot S shown in FIGS. 3 and 4.

As explained above, in an embodiment each pupil image 31 is acquired on at least one edge 32 of the target 30 of the substrate W. In the example shown in FIG. 5, each pupil image 31 is acquired at spot locations 33a, 33b on the two edges 32a, 32b of the target 30 extending in the Y-direction. Additionally, each pupil image 31 (i.e. the pupil image acquired at each focus setting of the metrology apparatus) is acquired at a spot location 33e in the centre of the target 30, i.e. between the edges 32a, 32b of the target 30.

Figure 6:
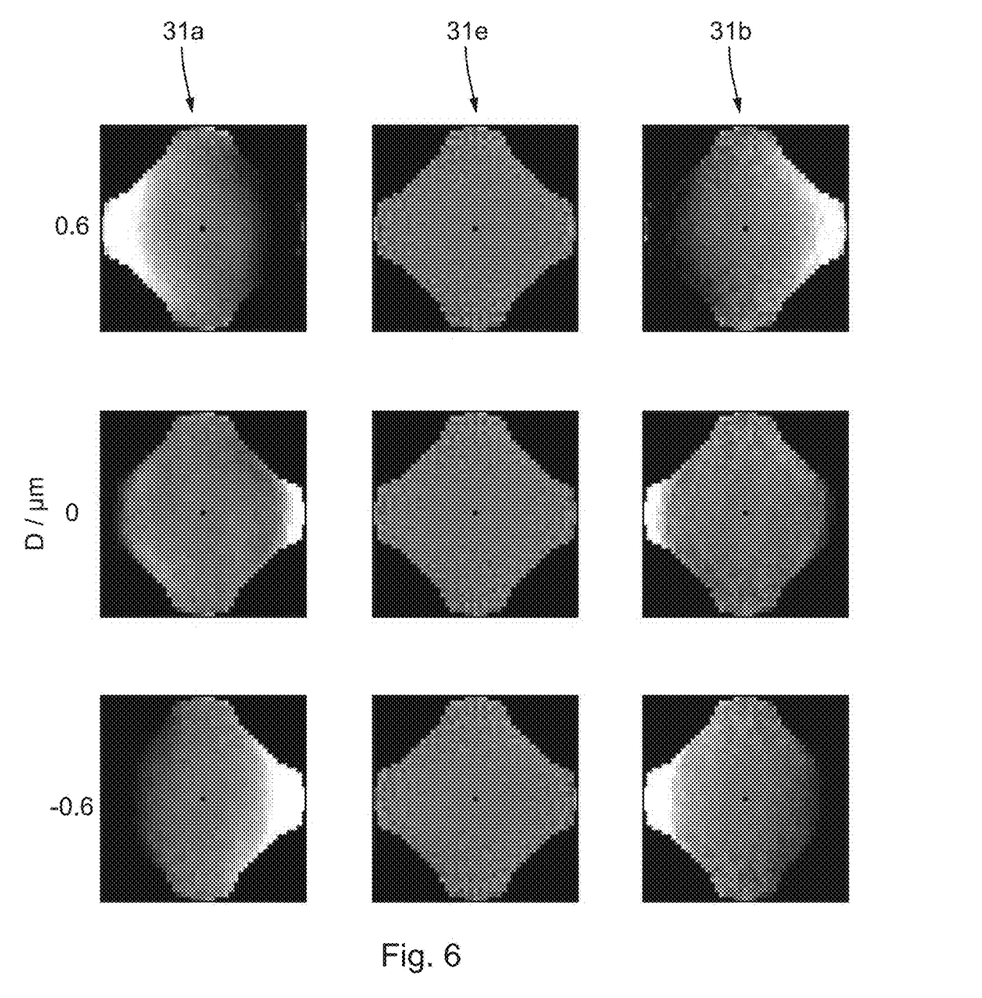
FIG. 6 shows the asymmetry in pupil images acquired at different focus settings and at different locations on the target.

FIG. 6 shows the pupil images 31 that were acquired. The left hand column in FIG. 6 represents the left hand edge pupil image 31a acquired at the different focus settings of the metrology apparatus. The central column in FIG. 6 represents the central pupil image 31e acquired at the central part of the target 30 at different focus settings of the metrology apparatus. The right hand column in FIG. 6 represents the right hand edge pupil image 31b acquired at the right hand edge 32b of the target 30 at different focus settings of the metrology apparatus. In FIG. 6, the different focus settings are represented by different values of defocus D, measured in microns in FIG. 6.

As can be seen generally in FIG. 6, there is a greater asymmetry in the pupil image 31 when the defocus D is greater. This indicates that the focus of the metrology apparatus represented by a zero value of the defocus D is not too far off the optimum focus setting off the metrology apparatus. However, the optimum focus setting of the metrology apparatus can be calculated more accurately.

In an embodiment, the method comprises calculating an asymmetry value AV for each acquired pupil image 31. The asymmetry value AV is representative of the asymmetry shown in each pupil image 31. Various methods of calculating the asymmetry value AV are possible. Merely as an example, the step of calculating the asymmetry value AV comprises summing intensity values of pixels in one half of the pupil image 31 and subtracting intensity values of pixels in the other half of the pupil image 31. This calculation step may be represented by the asymmetry formula shown below.

$$AV = \frac{\sum_{n=1}^{half\_pupil} (I_{pupil} - I_{point\ mirrored\ pupil})}{\sum_{n=1}^{pupil} I_{pupil}}$$

As shown in the above formula, in an embodiment the step of calculating the asymmetry value AV comprises normalising the asymmetry value AV according to the sum of the intensity values of all pixels in the whole pupil image 31. The calculated asymmetry value AV is then indicative of the asymmetry in the pupil image 31. The greater the asymmetry, the greater the asymmetry value AV.

Figure 7:
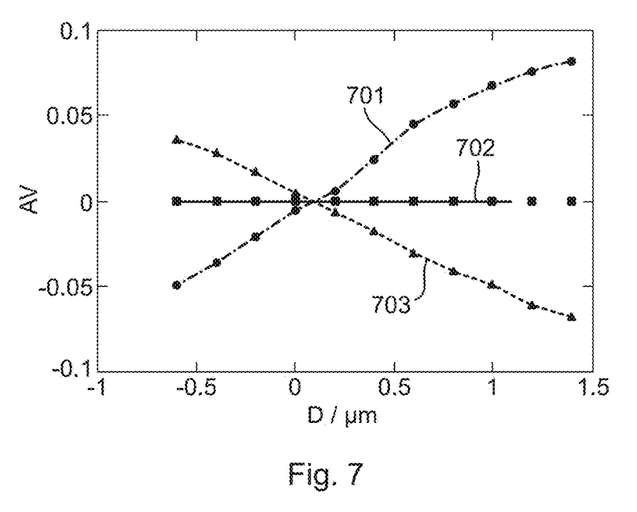
FIG. 7 is a graph showing the relationship between the focus setting of the metrology apparatus and the asymmetry in the pupil image for different locations on the target.

FIG. 7 is a graph showing the relationship between the focus setting of the metrology apparatus (represented by the value of defocus D) and the asymmetry value AV of the pupil image 31. The different lines 701-703 correspond to different locations on the target 30. In FIG. 7, the dot-chain line 701 connecting circular points corresponds to the left hand edge pupil image 31a. The solid line 702 connecting square points corresponds to the central pupil image 31e acquired at the centre of the target 30. The dashed line 703 connecting triangular points corresponds to the right hand edge pupil image 31b acquired at the right hand edge 32b of the target 30.

As shown in FIG. 7, the lines 701-703 corresponding to different locations on the target 30 cross each other. The lines 701-703 cross at the focus setting that provides the best focus of the illumination spot S of the metrology apparatus. In the example shown in FIG. 7, all three lines 701-703 cross at the same focus setting. However, it is not necessary to provide three lines. Instead, it would be possible to implement the invention by calculating only two lines. This could be done by, for example, acquiring each pupil image 31 at one edge 32 of the target and at the centre of the target 30, or by acquiring each pupil image 31 at two edges 32 of the target 30.

In a further alternative embodiment, the method could be implemented by acquiring each pupil image 31 at only one location of the target 30. In this case, the equivalent of the graph show in FIG. 7 would include only one single line. In this case, the best focus setting could be determined by calculating the focus setting for which the asymmetry value AV is zero. For example, the method could be implemented by acquiring each pupil image 31 at only one edge 32 of the target 30.

In an embodiment, the method comprises calculating a focus setting of the metrology apparatus corresponding to an asymmetry value AV of zero so as to determine a focus setting having an optimal focus. It may be that one of the focus settings for which a pupil image 31 was acquired provides an asymmetry value AV of zero. In this case, that focus setting may be determined as being the focus setting having an optimal focus. Alternatively, it may be that none of the focus settings for which a pupil image 31 was acquired corresponds to an asymmetry value AV of zero.

In an embodiment, the step of calculating the focus setting corresponding to an asymmetry value AV of zero comprises interpolating between calculated asymmetry values AV. For example, in the example shown in FIG. 7, the asymmetry value AV of zero is somewhere between the defocus D of zero and the defocus D of 0.2 μm. The focus setting corresponding to an asymmetry value AV of zero can be calculated by interpolating between these two calculated asymmetry values AV. It may be that the target 30 itself contains at least one overlay error. Optionally, the asymmetry value AV of the pupil image 31e measured at the centre of the target 30 can be used to compensate for any asymmetry in the target 30 itself.

In the example shown in FIG. 7, the optimal focus setting maybe calculated as a value of defocus D of 0.1 µm. For different applications (e.g. when the metrology apparatus is used to inspect other substrates W), the optimum focus setting of the metrology apparatus may be different. The present invention makes it possible to calibrate the focus of the metrology apparatus in an optimum way for each situation in which the metrology apparatus is used.

In an embodiment, the pupil image 31 is acquired using light having a polarisation direction. For example, the illumination light used by the metrology apparatus may be polarised in the Y-direction or in the X-direction. In an embodiment, the polarisation direction of the light of the metrology apparatus matches a direction in which the edge 32 of the target 30 extends. For example, in the diagram shown in FIG. 5, the edges 32a, 32b of the target 30 extend in the Y-direction. Accordingly, in an embodiment the pupil images 31 are acquired using light having a polarisation direction in the Y-direction.

Figure 8:
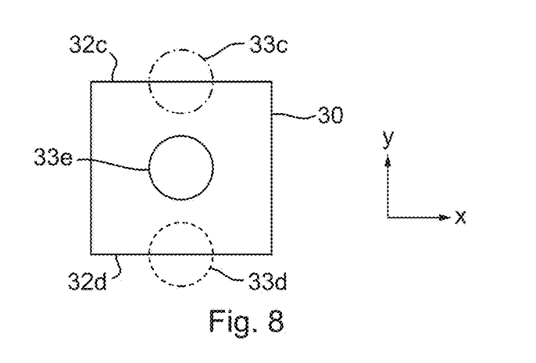
FIG. 8 is a diagram showing other locations on the target at which the pupil is measured according to an alternative embodiment of the invention.

FIG. 8 is a diagram of an alternative embodiment showing alternative locations at which pupil images 31 are acquired on the target 30. As shown in FIG. 8, pupil images 31 may be acquired at spot locations 33c, 33d at edges 32c, 32d of the target 30 that extend in the X-direction. In particular, a top edge pupil image 31c is acquired at the top edge 32c of the target 30. A bottom edge pupil image 31d is acquired at the bottom edge 32d of the target 30. A central pupil image 31e is acquired at a spot location 33e in a central portion of the target 30. The pupil images 31 may be acquired using light having a polarisation direction in the X-direction.

By matching the polarisation direction of the light to the direction in which the edges 32 of the target 30 extend, the effects of the polarisation direction on the acquired pupil image 31 can be reduced. The polarisation direction in the Y-direction may also be called the vertical polarisation direction. Hence, a vertically polarised sensing spot S may be used for the left and right positions of the target 30 shown in FIG. 5. The polarisation direction in the X-direction may also be called horizontal polarisation. A horizontally polarised sensing spot S maybe used for the top and bottom positions of the target (i.e. horizontal edges), as shown in FIG. 8.

The present invention provides an application-specific focus calibration for angular-resolved scatterometry. In an embodiment, the detection spot S is smaller than the size of the target 30. The target 30 is under-filled by the spot S. This is shown in FIGS. 5 and 8, where the central pupil image 31e is acquired using a sensing spot that fits entirely within the target 30.

In an embodiment, the target 30 has a diameter of at most 20 µm. In an embodiment the target 30 has a diameter of at most 10 µm, or optionally at most 5 µm. As an example, the target 30 may have a diameter of 4.5 µm. For example, the target 30 may be square, having a side length of 4.5 µm.

The present invention makes it possible to calibrate the focus of the metrology apparatus for a specific application more accurately. The method used for calibrating the focus of the metrology apparatus may comprise knife edge measurements. For example, the acquisition of pupil images 31 at the edges 32 of the target 30 shown in FIGS. 5 and 8 correspond to knife edge measurements. Although no knife edge is positioned as would be done in a traditional knife edge measurement, the optical properties in the two halves of the pupil image 31 are different. In particular, the optical properties (e.g. reflection property) of the target 30 are different from the optical properties of the region immediately outside of target 30. Accordingly, a knife edge measurement can be made, in which the acquired pupil image 31 has an asymmetry indicative of defocus of the illuminations spot S. These knife edge measurements are performed on the application to be measured (i.e. on the substrate W itself) instead of on the fiducial of the metrology apparatus. The calibration according to the invention can be called on target sensing to focus offset calibration. In an embodiment, the method comprises determining a focus correction per wavelength for the specific application.

By providing that the focus correction is optimised for the specific application, the optimal focus can be given more accurately. Furthermore, the edge 32 of the target 30 of the substrate 30 is sharper than the edge of the fiducial of the metrology apparatus. This improves the positioning of the sensing spot S. Furthermore, if the focus spot S is larger than the target 30, then any extra focus offset due to this will be accounted for in the calculated focus correction.

Optionally, each pupil image 31 is corrected for illumination and optics asymmetry before the asymmetry value AV is calculated. For each location on the target 30, the pupil image 31 is acquired using a plurality of different focus settings. The minimum number of different focus settings is two, so as to provide two points on the type of graph shown in FIG. 7 between which a line can be drawn. A greater number of focus settings used may improve the accuracy of the calculated optimal focus setting of the metrology apparatus.

In an embodiment, the asymmetry value AV is calculated using only the zeroth order illumination. This avoids adding any asymmetric parts that could otherwise undesirably contribute to the calculation of the focus correction. However, in an alternative embodiment higher orders may be used. Accordingly, corrections for asymmetry in illumination and optics may be applied for the higher orders.

In an embodiment, the determined focus setting is used for inspecting the substrate W throughout a die region adjacent to the target 30. For example, the target 30 may be positioned in the scribe lane adjacent to a die region of the substrate W. Once the target 30 has been used to calibrate the focus of the metrology apparatus, that calibrated focus setting may be used for the whole of that die region.

In an embodiment, a different target 30 is used to calibrate the focus of the metrology apparatus for each die region of the substrate W. Hence, for each of a plurality of die regions of the substrate W, a target 30 adjacent to the die region is used to determine a focus setting having the best focus.

However, in an alternative embodiment, one target 30 is used to calibrate the focus of the metrology apparatus, and that calibrated focus setting may be used for a plurality of die regions of the substrate W. In a further alternative embodiment, an adjustment is made to the determined focus setting (determined from using one target 30) so as to estimate as focus setting having the best focus for a die region of the substrate W distanced from the target 30.

Hence, the user may have information about how the optimal focus setting of the metrology apparatus varies across the substrate W. This may be known based on information about the layer thicknesses throughout the substrate W for example. This information can be used to make an adjustment to the focus calibration of the metrology apparatus. Accordingly, based on the focus calibration from one target 30, an optimal focus of the metrology apparatus can be determined throughout the substrate W, even for die regions that are distanced from (i.e. not adjacent to) the target 30.

Although specific reference may be made in this disclosure to the use of focus monitoring and control arrangements in inspection apparatuses such as scatterometers, it should be understood that the disclosed arrangements may have application in other types of functional apparatuses, as mentioned already above.

Although specific reference may be made in this text to the use of inspection apparatus in the manufacture of ICs, it should be understood that the inspection apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. Furthermore, parts of the apparatus may be implemented in the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

The invention claimed is:

1. A method for monitoring a characteristic of illumination from a metrology apparatus, the method comprising:
    acquiring, using the metrology apparatus, a set of pupil images at a location on a target on a substrate, wherein the location comprises an edge of the target; and
    calculating an asymmetry value for each pupil image of the set of pupil images,
    wherein the set of pupil images is acquired at different focus settings of the metrology apparatus.

2. The method of claim 1, further comprising:
    determining an optimal focus setting corresponding to an asymmetry value of zero.

3. The method of claim 2, wherein the determining the optimal focus setting comprises interpolating between calculated asymmetry values.

4. The method of claim 2, wherein the determined optimal focus setting is used for inspecting the substrate throughout a die region adjacent to the target.

5. The method of claim 2, wherein an adjustment is made to the determined optimal focus setting, based on known parameters of the substrate, and the adjustment is used for inspecting a die region of the substrate distanced from the target.

6. The method claim 1, wherein the calculating the asymmetry value comprises summing intensity values of pixels in one half of a pupil image from the set of pupil images and subtracting intensity values of pixels in the other half of the pupil image.

7. The method of claim 1, wherein the set of pupil images is acquired using light having a polarization direction that matches a direction in which the edge of the target extends.

8. The method of claim 1, wherein the set of pupil images is formed by illuminating the target with an illumination spot having a diameter of at most 20 µm.

9. The method of claim 1, wherein the target has a diameter of at most 20 µm.

10. The method of claim 1, wherein the target is positioned in a scribe lane of the substrate.

11. The method of claim 1, wherein a target adjacent to each die region of a plurality of regions of the substrate is used to determine a focus setting.

12. The method of claim 1, further comprising:
    acquiring, using the metrology apparatus, another set of pupil images at another location on the target, wherein the another location is different than the location; and
    calculating an asymmetry value for each pupil image of the another set of pupil images,
    wherein the another set of pupil images is acquired at least at some of the different focus settings of the metrology apparatus.

13. The method of claim 12, wherein the another location comprises:
    another edge of the target, wherein the another edge is different than the edge; or
    a position on the target such that an illumination spot fits entirely within the target so as not to include any edge of the target.

14. The method of claim 12, further comprising:
    determining a focus setting corresponding to an intersection of a line formed by data points of asymmetry values of the set of pupil images and a line formed by data points of asymmetry values of the another set of pupil images.

15. The method of claim 1, wherein the set of pupil images are formed by illuminating the target with an illumination spot having a diameter that, when positioned at the center of the target, under-fills the target.

16. A metrology apparatus, comprising:
    a measurement system configured to measure a parameter of a lithographic process and configured to:
        acquire a set of pupil images at a location on a target on a substrate, wherein the location comprises an edge of the target; and
        calculate an asymmetry value for each pupil image of the set of pupil images,
        wherein the set of pupil images is acquired at different focus settings of the metrology apparatus.

17. A non-transitory computer program product comprising machine-readable instructions configured to cause a processor to perform operations comprising:
    acquiring, using a metrology apparatus, a set of pupil images at a location on a target on a substrate, wherein the location comprises an edge of the target; and
    calculating an asymmetry value for each pupil image of the set of pupil images;
    wherein the set of pupil images is acquired at different focus settings of the metrology apparatus.

18. A system comprising:
an inspection apparatus configured to provide a radiation beam on a target on a substrate and to detect radiation diffracted by the target to determine a parameter of a patterning process; and
a non-transitory computer program product comprising machine-readable instructions configured to cause a processor to perform operations comprising:
acquiring, using the inspection apparatus, a set of pupil images at a location on the target, wherein the location comprises an edge of the target; and
calculating an asymmetry value for each pupil image of the set of pupil images,
wherein the set of pupil images is acquired at different focus settings of the inspection apparatus.

19. The system of claim 18, further comprising:
a lithographic apparatus comprising a support structure configured to hold a patterning device to modulate another radiation beam; and
a projection system arranged to project the modulated another radiation beam onto a the substrate.

* * * * *

UNITED STATES PATENT AND TRADEMARK OFFICE
CERTIFICATE OF CORRECTION

PATENT NO. : 10,317,805 B2
APPLICATION NO. : 15/842958
DATED : June 11, 2019
INVENTOR(S) : Schmetz-Schagen et al.

It is certified that error appears in the above-identified patent and that said Letters Patent is hereby corrected as shown below:

In the Claims

Column 16, Line 4, replace "The method claim 1," with --The method of claim 1,--.

Signed and Sealed this
Tenth Day of September, 2019

Andrei Iancu
*Director of the United States Patent and Trademark Office*